United States Patent
Burkholz

(10) Patent No.: US 11,890,139 B2
(45) Date of Patent: Feb. 6, 2024

(54) PORTABLE ULTRASOUND SYSTEMS

(71) Applicant: Bard Access Systems, Inc., Salt Lake City, UT (US)

(72) Inventor: Jonathan Karl Burkholz, Salt Lake City, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/466,832

(22) Filed: Sep. 3, 2021

(65) Prior Publication Data

US 2022/0061806 A1    Mar. 3, 2022

Related U.S. Application Data

(60) Provisional application No. 63/074,359, filed on Sep. 3, 2020.

(51) Int. Cl.
  *A61B 8/00* (2006.01)
  *A61B 17/34* (2006.01)

(52) U.S. Cl.
  CPC .......... *A61B 8/4427* (2013.01); *A61B 8/4455* (2013.01); *A61B 8/4472* (2013.01);
  (Continued)

(58) Field of Classification Search
  CPC ... A61B 8/4455; A61B 8/4427; A61B 8/4472; A61B 8/56; A61B 8/4444; A61B 8/4411; A61B 17/3403
  See application file for complete search history.

(56) References Cited

U.S. PATENT DOCUMENTS

| | | | |
|---|---|---|---|
| 5,148,809 | A | 9/1992 | Biegeleisen-Knight et al. |
| 5,181,513 | A | 1/1993 | Touboul et al. |
| | | (Continued) | |

FOREIGN PATENT DOCUMENTS

| | | | |
|---|---|---|---|
| EP | 0933063 A1 | 8/1999 | |
| EP | 1504713 A1 | 2/2005 | |
| | (Continued) | | |

OTHER PUBLICATIONS

Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).

(Continued)

*Primary Examiner* — Joel Lamprecht
*Assistant Examiner* — Nyrobi Celestine
(74) *Attorney, Agent, or Firm* — Rutan & Tucker LLP

(57) ABSTRACT

Disclosed herein are portable ultrasound systems and methods. In an example, a portable ultrasound system can include a handheld computer, a case holding the handheld computer, a probe head coupled to the case, and a communicating means for communicating between the probe head and the handheld computer. The handheld computer can include a display. The case can also include an anterior opening framing the display of the handheld computer. The case can include a rechargeable battery integrated into the case opposite the anterior opening. The probe head can include an array of ultrasonic transducers powered by the battery. In another example, a method of the portable ultrasound system includes a method of using the portable ultrasound system.

25 Claims, 5 Drawing Sheets

Figure 1C:
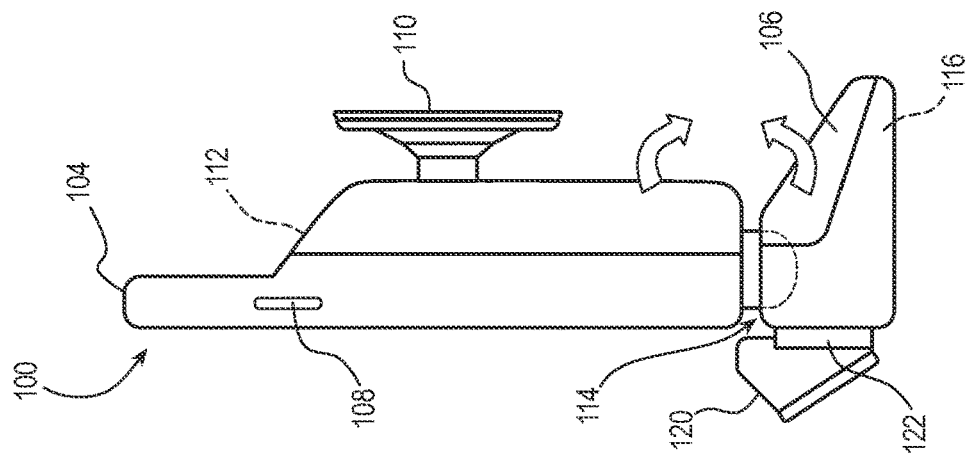

(52) U.S. Cl.
CPC ............ *A61B 8/4488* (2013.01); *A61B 8/461* (2013.01); *A61B 8/467* (2013.01); *A61B 8/56* (2013.01); *A61B 17/3403* (2013.01)

(56) References Cited

U.S. PATENT DOCUMENTS

| | | | |
|---|---|---|---|
| 5,325,293 A | 6/1994 | Dorne | |
| 5,441,052 A | 8/1995 | Miyajima | |
| 5,549,554 A | 8/1996 | Miraki | |
| 5,573,529 A | 11/1996 | Haak et al. | |
| 5,775,322 A | 7/1998 | Silverstein et al. | |
| 5,879,297 A | 3/1999 | Haynor et al. | |
| 5,908,387 A | 6/1999 | LeFree et al. | |
| 5,967,984 A | 10/1999 | Chu et al. | |
| 5,970,119 A | 10/1999 | Hofmann | |
| 6,004,270 A | 12/1999 | Urbano et al. | |
| 6,019,724 A | 2/2000 | Gronningsaeter et al. | |
| 6,068,599 A | 5/2000 | Saito et al. | |
| 6,074,367 A | 6/2000 | Hubbell | |
| 6,129,668 A | 10/2000 | Haynor et al. | |
| 6,132,379 A | 10/2000 | Patacsil et al. | |
| 6,216,028 B1 | 4/2001 | Haynor et al. | |
| 6,233,476 B1 | 5/2001 | Strommer et al. | |
| 6,245,018 B1 | 6/2001 | Lee | |
| 6,263,230 B1 | 7/2001 | Haynor et al. | |
| 6,375,615 B1 | 4/2002 | Flaherty et al. | |
| 6,436,043 B2 | 8/2002 | Bonnefous | |
| 6,498,942 B1 | 12/2002 | Esenaliev et al. | |
| 6,503,205 B2 | 1/2003 | Manor et al. | |
| 6,508,769 B2 | 1/2003 | Bonnefous | |
| 6,511,458 B2 | 1/2003 | Milo et al. | |
| 6,524,249 B2 | 2/2003 | Moehring et al. | |
| 6,543,642 B1 | 4/2003 | Milliorn | |
| 6,554,771 B1 | 4/2003 | Buil et al. | |
| 6,592,520 B1 | 7/2003 | Peszynski et al. | |
| 6,592,565 B2 | 7/2003 | Twardowski | |
| 6,601,705 B2 | 8/2003 | Molina et al. | |
| 6,612,992 B1 | 9/2003 | Hossack et al. | |
| 6,613,002 B1 | 9/2003 | Clark et al. | |
| 6,623,431 B1 | 9/2003 | Sakuma et al. | |
| 6,641,538 B2 | 11/2003 | Nakaya et al. | |
| 6,647,135 B2 | 11/2003 | Bonnefous | |
| 6,687,386 B1 | 2/2004 | Ito et al. | |
| 6,749,569 B1 | 6/2004 | Pellegretti | |
| 6,754,608 B2 | 6/2004 | Svanerudh et al. | |
| 6,755,789 B2 | 6/2004 | Stringer et al. | |
| 6,840,379 B2 | 1/2005 | Franks-Farah et al. | |
| 6,857,196 B2 | 2/2005 | Dalrymple | |
| 6,979,294 B1 | 12/2005 | Selzer et al. | |
| 7,074,187 B2 | 7/2006 | Selzer et al. | |
| 7,244,234 B2 | 7/2007 | Ridley et al. | |
| 7,359,554 B2 | 4/2008 | Klingensmith et al. | |
| 7,534,209 B2 | 5/2009 | Abend et al. | |
| 7,599,730 B2 | 10/2009 | Hunter et al. | |
| 7,637,870 B2 | 12/2009 | Flaherty et al. | |
| 7,681,579 B2 | 3/2010 | Schwartz | |
| 7,691,061 B2 | 4/2010 | Hirota | |
| 7,699,779 B2 | 4/2010 | Sasaki et al. | |
| 7,720,520 B2 | 5/2010 | Willis | |
| 7,727,153 B2 | 6/2010 | Fritz et al. | |
| 7,734,326 B2 | 6/2010 | Pedain et al. | |
| 7,831,449 B2 | 11/2010 | Ying et al. | |
| 7,905,837 B2 | 3/2011 | Suzuki | |
| 7,925,327 B2 | 4/2011 | Weese | |
| 7,927,278 B2 | 4/2011 | Selzer et al. | |
| 8,014,848 B2 | 9/2011 | Birkenbach et al. | |
| 8,060,181 B2 | 11/2011 | Rodriguez Ponce et al. | |
| 8,075,488 B2 | 12/2011 | Burton | |
| 8,090,427 B2 | 1/2012 | Eck et al. | |
| 8,105,239 B2 | 1/2012 | Specht | |
| 8,172,754 B2 | 5/2012 | Watanabe et al. | |
| 8,175,368 B2 | 5/2012 | Sathyanarayana | |
| 8,200,313 B1 | 6/2012 | Rambod et al. | |
| 8,211,023 B2 | 7/2012 | Swan et al. | |
| 8,228,347 B2 | 7/2012 | Beasley et al. | |
| 8,298,147 B2 | 10/2012 | Huennekens et al. | |
| 8,303,505 B2 | 11/2012 | Webler et al. | |
| 8,323,202 B2 | 12/2012 | Roschak et al. | |
| 8,328,727 B2 | 12/2012 | Miele et al. | |
| 8,388,541 B2 | 3/2013 | Messerly et al. | |
| 8,409,103 B2 | 4/2013 | Grunwald et al. | |
| 8,449,465 B2 | 5/2013 | Nair et al. | |
| 8,553,954 B2 | 10/2013 | Saikia | |
| 8,556,815 B2 | 10/2013 | Pelissier et al. | |
| 8,585,600 B2 | 11/2013 | Liu et al. | |
| 8,622,913 B2 | 1/2014 | Dentinger et al. | |
| 8,706,457 B2 | 4/2014 | Hart et al. | |
| 8,727,988 B2 | 5/2014 | Flaherty et al. | |
| 8,734,357 B2 | 5/2014 | Taylor | |
| 8,744,211 B2 | 6/2014 | Owen | |
| 8,754,865 B2 | 6/2014 | Merritt et al. | |
| 8,764,663 B2 | 7/2014 | Smok et al. | |
| 8,781,194 B2 | 7/2014 | Malek et al. | |
| 8,781,555 B2 | 7/2014 | Burnside et al. | |
| 8,790,263 B2 | 7/2014 | Randall et al. | |
| 8,849,382 B2 | 9/2014 | Cox et al. | |
| 8,939,908 B2 | 1/2015 | Suzuki et al. | |
| 8,961,420 B2 | 2/2015 | Zhang | |
| 9,022,940 B2 | 5/2015 | Meier | |
| 9,138,290 B2 | 9/2015 | Hadjicostis | |
| 9,204,858 B2 | 12/2015 | Pelissier et al. | |
| 9,220,477 B2 | 12/2015 | Urabe et al. | |
| 9,295,447 B2 | 3/2016 | Shah | |
| 9,320,493 B2 | 4/2016 | Visveshwara | |
| 9,357,980 B2 | 6/2016 | Toji et al. | |
| 9,364,171 B2 | 6/2016 | Harris et al. | |
| 9,427,207 B2 | 8/2016 | Sheldon et al. | |
| 9,445,780 B2 | 9/2016 | Hossack et al. | |
| 9,456,766 B2 | 10/2016 | Cox et al. | |
| 9,456,804 B2 | 10/2016 | Tamada | |
| 9,468,413 B2 | 10/2016 | Hall et al. | |
| 9,492,097 B2 | 11/2016 | Wilkes et al. | |
| 9,521,961 B2 | 12/2016 | Silverstein et al. | |
| 9,554,716 B2 | 1/2017 | Burnside et al. | |
| 9,582,876 B2 | 2/2017 | Specht | |
| 9,610,061 B2 | 4/2017 | Ebbini et al. | |
| 9,636,031 B2 | 5/2017 | Cox | |
| 9,649,037 B2 | 5/2017 | Lowe et al. | |
| 9,649,048 B2 | 5/2017 | Cox et al. | |
| 9,702,969 B2 | 7/2017 | Hope Simpson et al. | |
| 9,715,757 B2 | 7/2017 | Ng et al. | |
| 9,717,415 B2 | 8/2017 | Cohen et al. | |
| 9,731,066 B2 | 8/2017 | Liu et al. | |
| 9,814,433 B2 | 11/2017 | Benishti et al. | |
| 9,814,531 B2 | 11/2017 | Yagi et al. | |
| 9,861,337 B2 | 1/2018 | Patwardhan et al. | |
| 9,895,138 B2 | 2/2018 | Sasaki | |
| 9,913,605 B2 | 3/2018 | Harris et al. | |
| 9,949,720 B2 | 4/2018 | Southard et al. | |
| 10,043,272 B2 | 8/2018 | Forzoni et al. | |
| 10,449,330 B2 | 10/2019 | Newman et al. | |
| 10,524,691 B2 | 1/2020 | Newman et al. | |
| 10,751,509 B2 | 8/2020 | Misener | |
| 2002/0038088 A1 | 3/2002 | Imran et al. | |
| 2003/0047126 A1 | 3/2003 | Tomaschko | |
| 2003/0106825 A1 | 6/2003 | Molina et al. | |
| 2003/0120154 A1 | 6/2003 | Sauer et al. | |
| 2004/0055925 A1 | 3/2004 | Franks-Farah et al. | |
| 2005/0000975 A1 | 1/2005 | Carco et al. | |
| 2005/0049504 A1 | 3/2005 | Lo et al. | |
| 2005/0165299 A1 | 7/2005 | Kressy et al. | |
| 2005/0251030 A1 | 11/2005 | Azar et al. | |
| 2005/0267365 A1 | 12/2005 | Sokulin et al. | |
| 2006/0013523 A1 | 1/2006 | Childers et al. | |
| 2006/0015039 A1 | 1/2006 | Cassidy et al. | |
| 2006/0079781 A1 | 4/2006 | Germond-Rouet et al. | |
| 2006/0184029 A1 | 8/2006 | Haim et al. | |
| 2006/0210130 A1 | 9/2006 | Germond-Rouet et al. | |
| 2007/0038113 A1* | 2/2007 | Oonuki | A61B 8/4455 600/464 |
| 2007/0043341 A1 | 2/2007 | Anderson et al. | |
| 2007/0073155 A1 | 3/2007 | Park et al. | |
| 2007/0199848 A1 | 8/2007 | Ellswood et al. | |
| 2007/0239120 A1 | 10/2007 | Brock et al. | |

(56) References Cited

U.S. PATENT DOCUMENTS

| | | | |
|---|---|---|---|
| 2007/0249911 A1 | 10/2007 | Simon | |
| 2008/0009743 A1* | 1/2008 | Hayasaka | A61B 90/96 600/461 |
| 2008/0021322 A1 | 1/2008 | Stone et al. | |
| 2008/0033293 A1 | 2/2008 | Beasley et al. | |
| 2008/0033759 A1 | 2/2008 | Finlay | |
| 2008/0051657 A1 | 2/2008 | Rold | |
| 2008/0146915 A1 | 6/2008 | McMorrow | |
| 2008/0177186 A1 | 7/2008 | Slater et al. | |
| 2008/0221425 A1 | 9/2008 | Olson et al. | |
| 2008/0294037 A1 | 11/2008 | Richter | |
| 2008/0300491 A1 | 12/2008 | Bonde et al. | |
| 2009/0012399 A1 | 1/2009 | Sunagawa et al. | |
| 2009/0143672 A1 | 6/2009 | Harms et al. | |
| 2009/0143684 A1 | 6/2009 | Cermak et al. | |
| 2009/0156926 A1 | 6/2009 | Messerly et al. | |
| 2009/0306509 A1 | 12/2009 | Pedersen et al. | |
| 2010/0016726 A1* | 1/2010 | Meier | A61B 8/0841 600/459 |
| 2010/0177182 A1* | 7/2010 | Kagenow | A61B 5/489 348/E7.085 |
| 2010/0211026 A2 | 8/2010 | Sheetz et al. | |
| 2010/0286515 A1 | 11/2010 | Gravenstein et al. | |
| 2010/0312121 A1 | 12/2010 | Guan | |
| 2011/0002518 A1 | 1/2011 | Ziv-Ari et al. | |
| 2011/0071404 A1 | 3/2011 | Schmitt et al. | |
| 2011/0275930 A1* | 11/2011 | Jho | A61M 5/14276 604/288.01 |
| 2011/0313293 A1 | 12/2011 | Lindekugel et al. | |
| 2012/0088991 A1* | 4/2012 | Nachabe | A61B 6/469 600/411 |
| 2012/0179038 A1 | 7/2012 | Meurer et al. | |
| 2012/0197132 A1 | 8/2012 | O'Connor | |
| 2012/0220865 A1 | 8/2012 | Brown et al. | |
| 2012/0277576 A1 | 11/2012 | Lui | |
| 2013/0041250 A1 | 2/2013 | Pelissier et al. | |
| 2013/0102889 A1 | 4/2013 | Southard et al. | |
| 2013/0131499 A1 | 5/2013 | Chan et al. | |
| 2013/0131502 A1 | 5/2013 | Blaivas et al. | |
| 2013/0150724 A1 | 6/2013 | Blaivas et al. | |
| 2013/0188832 A1 | 7/2013 | Ma et al. | |
| 2013/0218024 A1 | 8/2013 | Boctor et al. | |
| 2014/0005530 A1 | 1/2014 | Liu et al. | |
| 2014/0073976 A1 | 3/2014 | Fonte et al. | |
| 2014/0100440 A1 | 4/2014 | Cheline et al. | |
| 2014/0180098 A1 | 6/2014 | Flaherty et al. | |
| 2014/0188133 A1 | 7/2014 | Misener | |
| 2014/0188440 A1 | 7/2014 | Donhowe et al. | |
| 2014/0276059 A1 | 9/2014 | Sheehan | |
| 2014/0276081 A1 | 9/2014 | Tegels | |
| 2014/0276085 A1 | 9/2014 | Miller | |
| 2014/0276690 A1 | 9/2014 | Grace | |
| 2014/0343431 A1 | 11/2014 | Vajinepalli et al. | |
| 2015/0005738 A1 | 1/2015 | Blacker | |
| 2015/0011887 A1 | 1/2015 | Ahn et al. | |
| 2015/0065916 A1 | 3/2015 | Maguire et al. | |
| 2015/0073279 A1 | 3/2015 | Cai et al. | |
| 2015/0112200 A1 | 4/2015 | Oberg et al. | |
| 2015/0190111 A1* | 7/2015 | Fry | A61B 8/4209 600/438 |
| 2015/0209113 A1 | 7/2015 | Burkholz et al. | |
| 2015/0209526 A1 | 7/2015 | Matsubara et al. | |
| 2015/0265769 A1* | 9/2015 | Bratbak | A61N 1/372 604/95.01 |
| 2015/0297097 A1 | 10/2015 | Matsubara et al. | |
| 2015/0359991 A1 | 12/2015 | Dunbar et al. | |
| 2016/0029995 A1 | 2/2016 | Navratil et al. | |
| 2016/0113699 A1 | 4/2016 | Sverdlik et al. | |
| 2016/0120607 A1 | 5/2016 | Sorotzkin et al. | |
| 2016/0166232 A1 | 6/2016 | Merritt | |
| 2016/0202053 A1 | 7/2016 | Walker et al. | |
| 2016/0213398 A1 | 7/2016 | Liu | |
| 2016/0278869 A1 | 9/2016 | Grunwald | |
| 2016/0296208 A1 | 10/2016 | Sethuraman et al. | |
| 2016/0374644 A1 | 12/2016 | Mauldin, Jr. et al. | |
| 2017/0007200 A1* | 1/2017 | Hagy | A61B 8/0841 |
| 2017/0079548 A1 | 3/2017 | Silverstein et al. | |
| 2017/0164923 A1 | 6/2017 | Matsumoto | |
| 2017/0215842 A1 | 8/2017 | Ryu et al. | |
| 2017/0303889 A1* | 10/2017 | Grim | A61B 10/0266 |
| 2017/0367678 A1 | 12/2017 | Sirtori et al. | |
| 2018/0014811 A1* | 1/2018 | Sonnenschein | A61B 8/565 |
| 2018/0015256 A1 | 1/2018 | Southard et al. | |
| 2018/0116723 A1 | 5/2018 | Hettrick et al. | |
| 2018/0125450 A1 | 5/2018 | Blackbourne et al. | |
| 2018/0161502 A1 | 6/2018 | Nanan et al. | |
| 2018/0199914 A1 | 7/2018 | Ramachandran et al. | |
| 2018/0214119 A1 | 8/2018 | Mehrmohammadi et al. | |
| 2018/0228465 A1 | 8/2018 | Southard et al. | |
| 2018/0310955 A1* | 11/2018 | Lindekugel | A61B 90/98 |
| 2018/0356493 A1* | 12/2018 | Stapert | A61B 34/20 |
| 2019/0125470 A1* | 5/2019 | Moskowitz | A61B 17/3401 |
| 2019/0365348 A1 | 12/2019 | Toume et al. | |
| 2019/0374201 A1* | 12/2019 | Griffith | A61B 8/4483 |
| 2020/0113540 A1 | 4/2020 | Gijsbers et al. | |
| 2020/0305927 A1* | 10/2020 | Grim | A61B 8/4444 |
| 2020/0390416 A1* | 12/2020 | Swan | A61B 8/12 |
| 2022/0039777 A1 | 2/2022 | Durfee | |
| 2022/0096797 A1 | 3/2022 | Prince | |
| 2022/0104886 A1 | 4/2022 | Blanchard et al. | |
| 2022/0117582 A1 | 4/2022 | McLaughlin et al. | |
| 2022/0160434 A1 | 5/2022 | Messerly et al. | |
| 2022/0313363 A1* | 10/2022 | Brahmstedt | A61B 8/4254 |

FOREIGN PATENT DOCUMENTS

| | | | |
|---|---|---|---|
| EP | 1591074 B1 | 5/2008 | |
| EP | 3181083 A1 | 6/2017 | |
| EP | 2900131 B1 * | 7/2019 | A61B 17/3403 |
| JP | 2000271136 A | 10/2000 | |
| JP | 2018175547 A | 11/2018 | |
| KR | 20180070878 A | 6/2018 | |
| WO | 2013059714 A1 | 4/2013 | |
| WO | 2014/115150 A1 | 7/2014 | |
| WO | 2015/017270 A1 | 2/2015 | |
| WO | 2017096487 A1 | 6/2017 | |
| WO | 2017214428 A1 | 12/2017 | |
| WO | 2018/026878 A1 | 2/2018 | |
| WO | 2018134726 A1 | 7/2018 | |
| WO | 2019/232451 A1 | 12/2019 | |
| WO | 2020/002620 A1 | 1/2020 | |
| WO | 2020/016018 A1 | 1/2020 | |
| WO | 2019/232454 A9 | 2/2020 | |
| WO | 2020/044769 A1 | 3/2020 | |
| WO | 2020/186198 A1 | 9/2020 | |
| WO | 2022/072727 A2 | 4/2022 | |
| WO | 2022/081904 A1 | 4/2022 | |

OTHER PUBLICATIONS

PCT/US2021/045218 filed Aug. 9, 2021 International Search Report and Written Opinion dated Nov. 23, 2021.

PCT/US2021/049123 filed Sep. 3, 2021 International Search Report and Written Opinion dated May 16, 2022.

PCT/US2021/053018 filed Sep. 30, 2021 International Search Report and Written Opinion dated May 3, 2022.

PCT/US2021/060622 filed Nov. 23, 2021 International Search Report and Written Opinion dated Mar. 3, 2022.

PCT/US2021/061267 filed Nov. 30, 2021 International Search Report and Written Opinion dated Mar. 9, 2022.

PCT/US2021/061276 filed Nov. 30, 2021 International Search Report and Written Opinion dated Mar. 9, 2022.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.

U.S. Appl. No. 15/951,903, filed Apr. 12, 2018 Board Decision dated Apr. 20, 2022.

U.S. Appl. No. 15/951,903, filed Apr. 12, 2018 Notice of Allowance dated May 2, 2022.

(56) References Cited

OTHER PUBLICATIONS

William F Garrett et al: "Real-time incremental visualization of dynamic ultrasound vols. using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.
Pagoulatos, N. et al. "New spatial localizer based on fiber optics with applications in 3D ultrasound imaging" Proceeding of Spie, vol. 3976 (Apr. 18, 2000; Apr. 18, 2000).
PCT/US12/61182 International Seach Report and Written Opinion dated Mar. 11, 2013.
PCT/US2021/049123 filed Sep. 3, 2021 International Search Report and Written Opinion dated Feb. 4, 2022.
PCT/US2021/049294 filed Sep. 7, 2021 International Search Report and Written Opinion dated Dec. 8, 2021.
PCT/US2021/049712 filed Sep. 9, 2021 International Search Report and Written Opinion dated Dec. 14, 2021.
PCT/US2021/052055 filed Sep. 24, 2021 International Search Report and Written Opinion dated Dec. 20, 2021.
U.S. Appl. No. 13/656,563, filed Oct. 19, 2012 Decision on Appeal dated Nov. 1, 2017.
U.S. Appl. No. 13/656,563, filed Oct. 19, 2012 Examiner's Answer dated Nov. 16, 2015.
U.S. Appl. No. 13/656,563, filed Oct. 19, 2012 Final Office Action dated Dec. 5, 2014.
U.S. Appl. No. 13/656,563, filed Oct. 19, 2012 Non-Final Office Action dated Jul. 18, 2014.
U.S. Appl. No. 15/650,474, filed Jul. 14, 2017 Final Office Action dated Jun. 2, 2020.
U.S. Appl. No. 15/650,474, filed Jul. 14, 2017 Non-Final Office Action dated Dec. 16, 2019.
U.S. Appl. No. 15/650,474, filed Jul. 14, 2017 Notice of Allowance dated Dec. 11, 2020.
U.S. Appl. No. 15/650,474, filed Jul. 14, 2017 Notice of Allowance dated Mar. 1, 2021.
U.S. Appl. No. 15/951,903, filed Apr. 12, 2018 Advisory Action dated Dec. 22, 2020.
U.S. Appl. No. 15/951,903, filed Apr. 12, 2018 Examiner's Answer dated Jun. 3, 2021.
U.S. Appl. No. 15/951,903, filed Apr. 12, 2018 Final Office Action dated Oct. 13, 2020.
U.S. Appl. No. 15/951,903, filed Apr. 12, 2018 Non-Final Office Action dated May 22, 2020.
U.S. Appl. No. 17/020,476, filed Sep. 14, 2020 Non-Final Office Action dated Feb. 9, 2022.

\* cited by examiner

PORTABLE ULTRASOUND SYSTEMS

PRIORITY

This application claims the benefit of priority to U.S. Provisional Patent Application No. 63/074,359, filed Sep. 3, 2020, which is incorporated by reference in its entirety into this application.

BACKGROUND

A range of ultrasound systems exist including those with wired or wireless ultrasound probes connected to relatively large visual displays. These systems require, for example, a clinician to hold and manipulate an ultrasound probe with one hand while positioning and placing a vascular access device ("VAD") in an insertion site of a patient with another hand. Meanwhile, the clinician might need to look away from the insertion site toward a relatively large visual display that is typically positioned across from the patient. Such an arrangement is not intuitive nor easy to master for clinicians. Other ultrasound systems include wired ultrasound probes connected to smartphones such as those of Butterfly Network Inc. of New York City, N.Y. Although such systems are more portable, they require use of both hands, which still makes it a difficult for a clinician when placing a VAD, as one hand is required to hold and manipulate the ultrasound probe while the other hand is used to hold the smartphone connected to the ultrasound probe. Other ultrasound systems include portable ultrasound systems including ultrasound probes with onboard displays, but these systems lack critically important data-input functionality, video-recording capability, needle-tracking capability, etc.

Disclosed herein are portable ultrasound systems and methods that address at least the foregoing.

SUMMARY

Disclosed herein is a portable ultrasound probe including, in some embodiments, a case configured to hold a handheld computer, a probe head coupled to the case, and a communicating means for communicating between the probe head and the handheld computer. The case includes an anterior opening configured to frame a display of the handheld computer. The case also includes a rechargeable battery integrated into the case opposite the anterior opening. The probe head includes an array of ultrasonic transducers powered by the battery.

In some embodiments, the case includes one or more side buttons configured to overlie one or more side buttons of the handheld computer. The one-or-more side buttons of the case are configured to mechanically transfer button presses to the one-or-more side buttons of the handheld computer.

In some embodiments, the case includes a handle incorporated into the case opposite the anterior opening. The handle is configured to facilitate holding the portable ultrasound probe or moving the portable ultrasound probe over skin of a patient with a single hand.

In some embodiments, the handle includes a knob, one or more finger loops, or an adjustable hand strap.

In some embodiments, the case includes a posterior opening framing a camera of the handheld computer.

In some embodiments, the probe head is removably coupled to the case.

In some embodiments, the probe head is fixedly coupled to the case.

In some embodiments, the probe head is configured to articulate about a joint coupling the probe head to the case.

In some embodiments, the portable ultrasound probe further includes a needle guide coupled to a needle-guide holder of the probe head.

In some embodiments, the communicating means for communicating between the probe head and the handheld computer is a wireless module disposed in the probe head for wireless communications with the handheld computer.

In some embodiments, the communicating means for communicating between the probe head and the handheld computer is a bus between the probe head and a connector disposed in the case for connecting the handheld computer.

Also disclosed herein is a portable ultrasound system including, in some embodiments, a handheld computer, a case holding the handheld computer, a probe head coupled to the case, and a communicating means for communicating between the probe head and the handheld computer. The handheld computer includes a display. The case includes an anterior opening framing the display of the handheld computer. The case also includes a rechargeable battery integrated into the case opposite the anterior opening. The probe head includes an array of ultrasonic transducers powered by the battery.

In some embodiments, the case includes one or more side buttons overlying one or more side buttons of the handheld computer. The one-or-more side buttons of the case are configured to mechanically transfer button presses to the one-or-more side buttons of the handheld computer.

In some embodiments, the case includes a handle incorporated into the case opposite the anterior opening. The handle is configured to facilitate holding the portable ultrasound system or moving the portable ultrasound system and the probe head thereof over skin of a patient with a single hand.

In some embodiments, the handle includes a knob, one or more finger loops, or an adjustable hand strap.

In some embodiments, the case includes a posterior opening configured to frame a camera of the handheld computer.

In some embodiments, the probe head is removably coupled to the case.

In some embodiments, the probe head is fixedly coupled to the case.

In some embodiments, the probe head is configured to articulate about a joint coupling the probe head to the case.

In some embodiments, the portable ultrasound system further includes a needle guide coupled to the probe head.

In some embodiments, the communicating means for communicating between the probe head and the handheld computer is a wireless module disposed in the probe head for wireless communications with a wireless module disposed in the handheld computer.

In some embodiments, the handheld computer is removable.

In some embodiments, the handheld computer is a smartphone including one or more programs or modules thereof configured to drive the ultrasonic transducers as well as process reflected ultrasound signals received by the ultrasonic transducers into ultrasound images for display on a display screen of the display.

In some embodiments, the handheld computer is a dedicated device configured to drive the ultrasonic transducers as well as process reflected ultrasound signals received by the ultrasonic transducers into ultrasound images for display on a display screen of the display.

In some embodiments, the communicating means for communicating between the probe head and the handheld computer is a bus between the probe head and a connector disposed in the case for connecting the handheld computer when disposed in the case.

In some embodiments, the handheld computer is integral. The handheld computer is a dedicated device configured to drive the ultrasonic transducers as well as process reflected ultrasound signals received by the ultrasonic transducers into ultrasound images for display on a display screen of the display.

In some embodiments, the communicating means for communicating between the probe head and the handheld computer is a bus between the probe head and the handheld computer.

In some embodiments, the portable ultrasound system further includes a charging cradle configured to charge the battery.

Also disclosed herein is a method of a portable ultrasound system. The method includes, in some embodiments, an obtaining step, a moving step, and a monitoring step. The obtaining step includes obtaining the portable ultrasound system. The portable ultrasound system includes a handheld computer including a display, a case holding the handheld computer, and a probe head coupled to the case. The moving step includes moving the probe head of the portable ultrasound system over skin of a patient. While performing the moving step, the probe head emits generated ultrasound signals into the patient from an array of ultrasonic transducers in the probe head and receives reflected ultrasound signals from the patient by the array of ultrasonic transducers. The monitoring step includes monitoring ultrasound images on a display screen of the display.

In some embodiments, the method further includes a replacing step. The replacing step includes removing the probe head from the case and coupling another probe head to the case.

In some embodiments, the moving step includes moving the probe head with a single hand. The case includes a handle selected from a knob, one or more finger loops, and an adjustable strap configured to facilitate holding the portable ultrasound system or moving the probe head thereof over the skin of the patient with the single hand.

In some embodiments, the moving step includes allowing the probe head to articulate about a joint coupling the probe head to the case while moving the probe head over the skin of the patient.

In some embodiments, the method further includes a pressing step. The pressing step includes pressing a side button of one or more side buttons of the case to switch between longitudinal and transverse scanning when the array of ultrasonic transducers is a 2-dimensional ("2D") array of ultrasonic transducers.

In some embodiments, the method further comprises an attaching step. The attaching step includes attaching a needle guide to a needle-guide holder of the probe head. The needle guide includes a needle through hole configured to direct the needle into the patient under the probe head.

In some embodiments, the method further comprises a creating step. The creating step includes identifying an anatomical target of the patient and inserting the needle into the anatomical target, thereby creating an access site.

In some embodiments, the method further includes an imaging step. The imaging step included imaging the skin of the patient through a posterior opening of the case with a camera of the handheld computer after identifying the anatomical target thereunder and before inserting the needle in the anatomical target.

In some embodiments, the method further includes another monitoring step. The other monitoring step includes monitoring on-screen guidance of the needle on a display screen of the display. The probe head further includes an array of magnetic sensors configured to detect changes in a magnetic field, when the needle is magnetized, for the on-screen guidance.

In some embodiments, the method further includes a placing step. The placing step includes placing the portable ultrasound system in a charging cradle to charge a battery integrated into the case of the portable ultrasound system.

These and other features of the concepts provided herein will become more apparent to those of skill in the art in view of the accompanying drawings and following description, which describe particular embodiments of such concepts in greater detail.

DRAWINGS

Figure 1B:
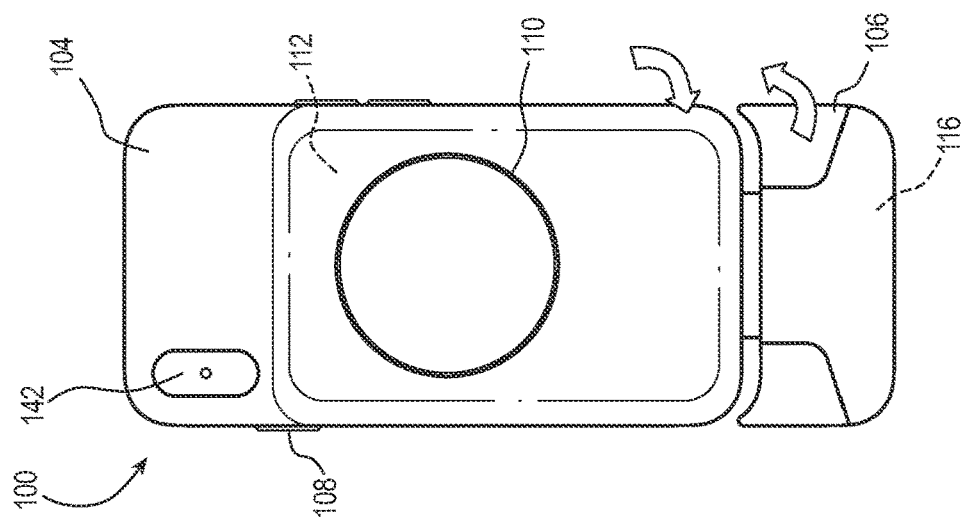
Figure 1A:
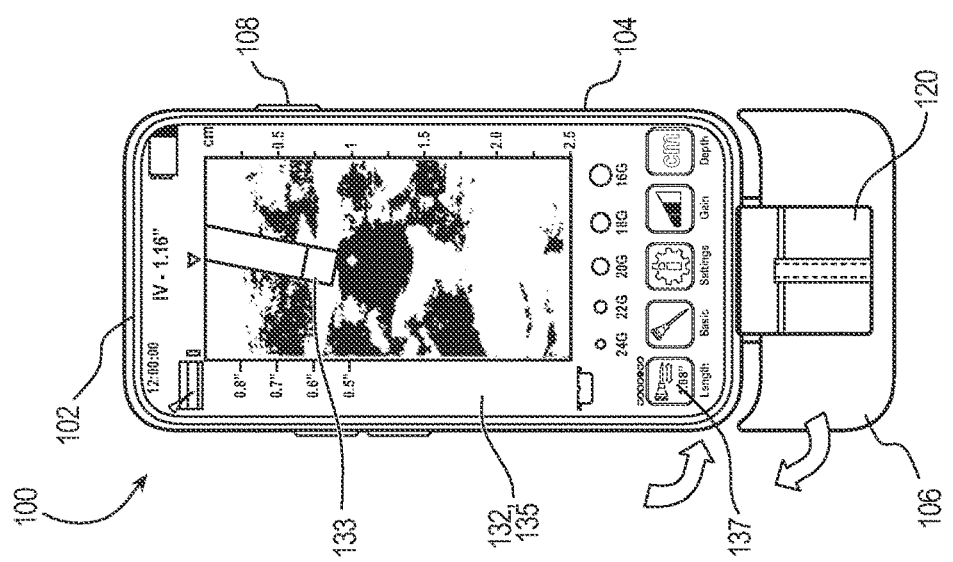

FIG. 1A provides a front view of a portable ultrasound system including a handheld computer in a case with a removably coupled probe head coupled thereto in accordance with some embodiments.

FIG. 1B provides a back view of the portable ultrasound system of FIG. 1A in accordance with some embodiments.

FIG. 1C provides a side view of the portable ultrasound system of FIG. 1A in accordance with some embodiments.

Figure 2C:
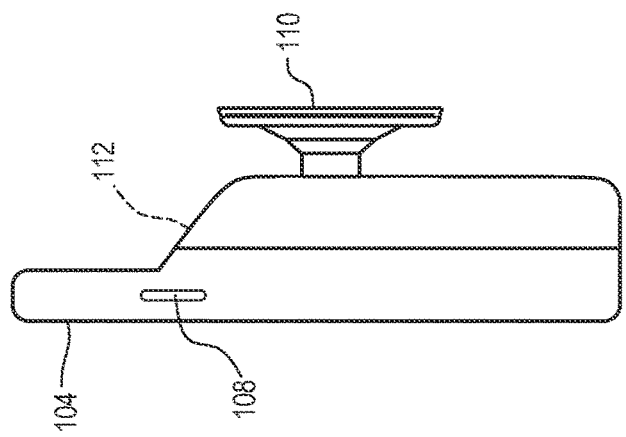
Figure 2B:
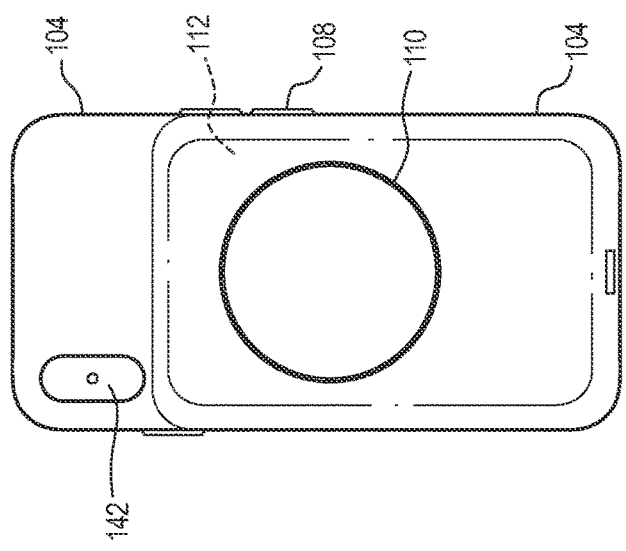
Figure 2A:
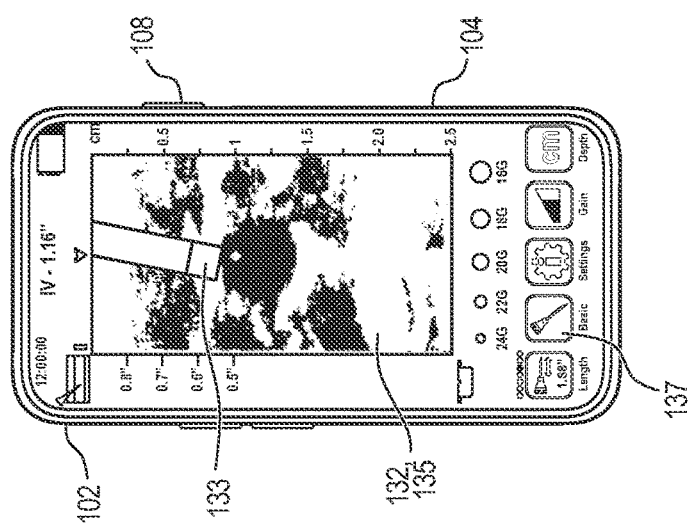

FIG. 2A provides a front view of the portable ultrasound system of FIG. 1A without the probe head in accordance with some embodiments.

FIG. 2B provides a back view of the portable ultrasound system of FIG. 1A without the probe head in accordance with some embodiments.

FIG. 2C provides a side view of the portable ultrasound system of FIG. 1A without the probe head in accordance with some embodiments.

Figure 3C:
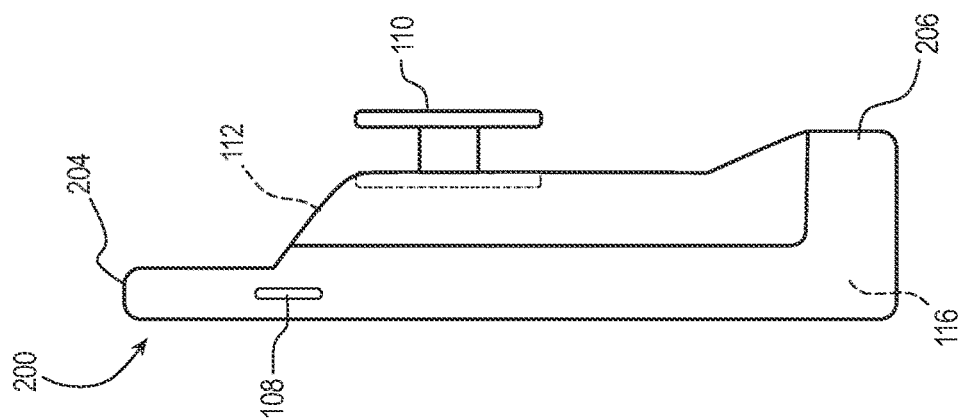
Figure 3B:
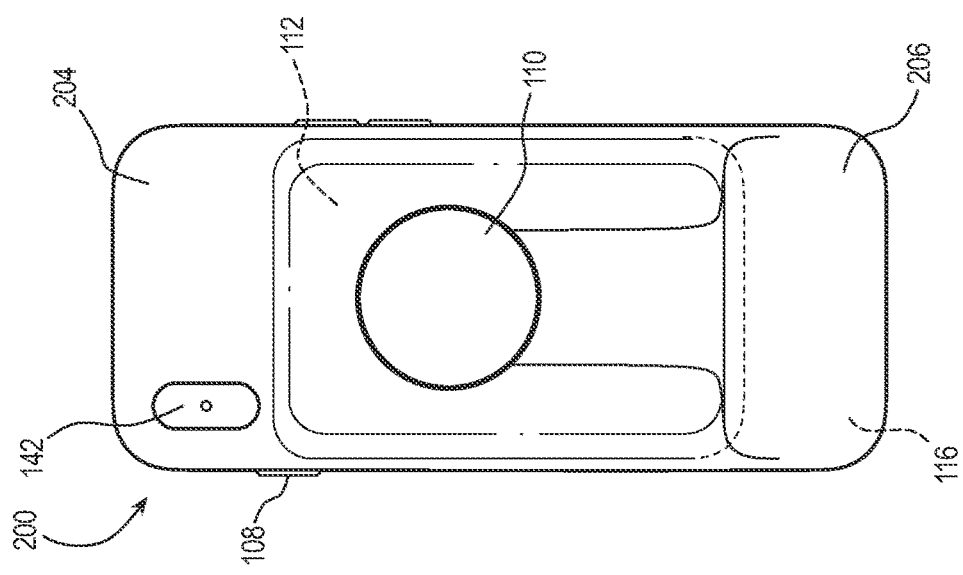
Figure 3A:
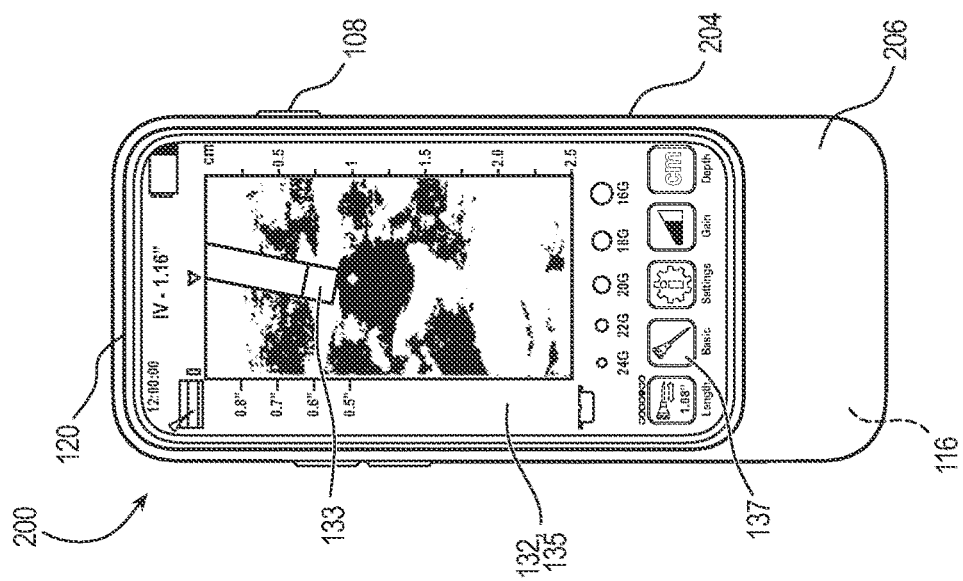

FIG. 3A provides a front view of a portable ultrasound system including a handheld computer in a case with a fixedly coupled probe head coupled thereto in accordance with some embodiments.

FIG. 3B provides a back view of the portable ultrasound system of FIG. 3A in accordance with some embodiments.

FIG. 3C provides a side view of the portable ultrasound system of FIG. 3A in accordance with some embodiments.

Figure 4C:
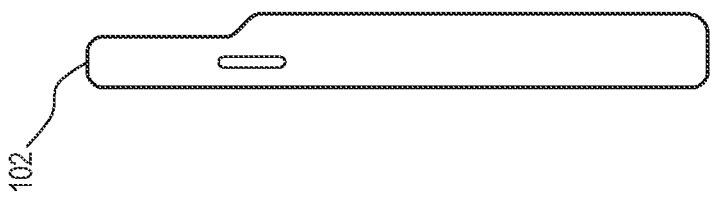
Figure 4B:
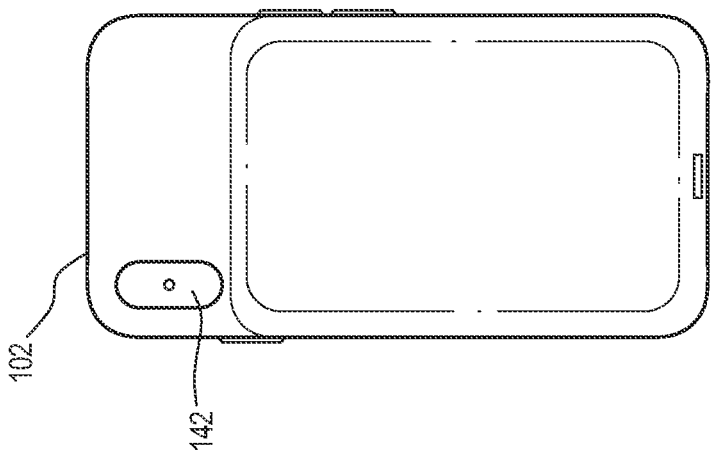
Figure 4A:
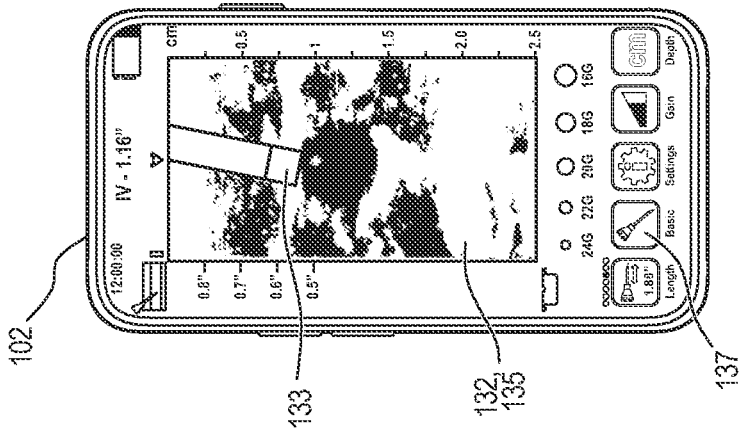

FIG. 4A provides a front view of the handheld computer of the portable ultrasound system of either FIG. 1A or 3A in accordance with some embodiments.

FIG. 4B provides a back view of the handheld computer of the portable ultrasound system of FIG. 1A or 3A in accordance with some embodiments.

FIG. 4C provides a side view of the handheld computer of the portable ultrasound system of FIG. 1A or 3A in accordance with some embodiments.

Figure 5:
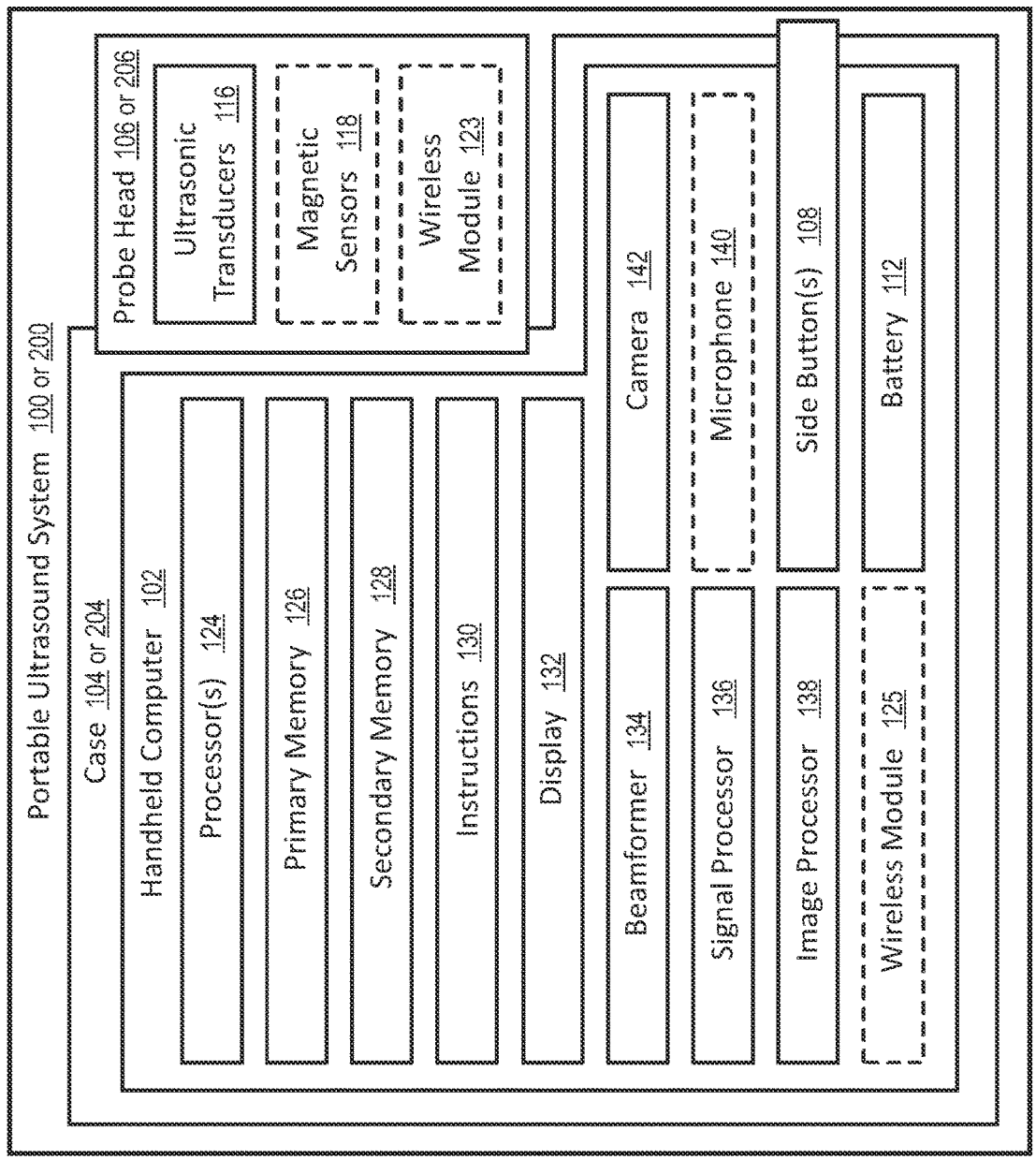

FIG. 5 provides a block diagram of the portable ultrasound system of either FIG. 1A or 3A in accordance with some embodiments.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Lastly, in the following description, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

Unless defined otherwise, all technical and scientific terms used herein have the same meaning as commonly understood by those of ordinary skill in the art.

As set forth above, a range of ultrasound systems exist; however, the existing ultrasound systems include various deficiencies following from their design. Disclosed herein are portable ultrasound systems and methods that address the foregoing deficiencies.

Portable Ultrasound Systems

FIGS. 1A-1C and 2A-2C provide views of a portable ultrasound system 100 including a handheld computer 102 in a case 104 respectively with and without a removably coupled probe head 106 in accordance with some embodiments. FIGS. 3A-3C provide views of a portable ultrasound system 200 including the handheld computer 102 in a case 204 with a fixedly coupled probe head 206 in accordance with some embodiments. FIGS. 4A-4C provide views of the handheld computer 102 of the portable ultrasound system 100 or 200 in accordance with some embodiments in which the handheld computer 102 is removable. FIG. 5 provides a block diagram of the portable ultrasound system 100 or 200 in accordance with some embodiments.

The portable ultrasound system 100 or 200 includes a portable ultrasound probe and the handheld computer 102, which handheld computer 102 can be integral with the portable ultrasound probe or removable therefrom. The description set forth below generally begins with the portable ultrasound probe, the case 104 or 204 of which is configured to accept the removable handheld computer 102 when inserted therein and, thereby, form the portable ultrasound system 100 or 200. (Said differently, the portable ultrasound probe is the portable ultrasound system 100 or 200 without the handheld computer 102.) However, description for the portable ultrasound system 100 or 200 including the integral or removable handheld computer 102 is provided where contextually convenient. Subsequent description is generally directed to the handheld computer 102 and the portable ultrasound system 100 or 200, itself, whether or not the handheld computer 102 is integral with the portable ultrasound system 100 or 200 or removable therefrom.

The portable ultrasound probe includes the case 104 or 204 configured to hold the handheld computer 102, the probe head 106 or 206 coupled to the case 104 or 204, and a communicating means for communicating between the probe head 106 or 206 and the handheld computer 102.

The case 104 or 204 can include one or more openings to accommodate one or more features of the handheld computer 102 while holding the handheld computer 102 therein. In an example, the one-or-more openings can include an anterior opening configured to frame the front-facing display 132 of the handheld computer 102 when the handheld computer 102 is held in the case 104 or 204. In another example, the one-or-more openings can include a posterior opening configured to frame the rear-facing camera 142 of the handheld computer 102 when the handheld computer 102 is held in the case 104 or 204.

The case 104 or 204 can include one or more side buttons 108 configured for providing data or control signals to the handheld computer 102 via button presses. For example, the one-or-more side buttons 108 can provide control signals when pressed for switching between longitudinal or transverse scanning with a two-dimensional ("2D") array of ultrasonic transducers in, for example, the probe head 206. The one-or-more side buttons 108 can be in direct communication with the handheld computer 102 when the handheld computer 102 is integral with the case 104 or 204. That said, the one-or-more side buttons 108 can be in indirect communication with the handheld computer 102 when the handheld computer 102 is removable. Indeed, the one-or-more side buttons 108 can overlie one or more side buttons of the handheld computer 102. In such embodiments, the one-or-more side buttons 108 of the case104 or 204 are configured to mechanically transfer button presses to the one-or-more side buttons of the handheld computer 102.

The case 104 or 204 can include a handle 110 incorporated into the case 104 or 204 opposite the anterior opening. The handle 110 is configured to facilitate holding the portable ultrasound system 100 or 200 or moving the probe head 106 or 206 thereof over skin of a patient with a single hand, left or right, in view of the handle 110 preferably being symmetrical. Indeed, the handle 110 in combination with a relatively small form factor enables the portable ultrasound system 100 or 200 to be held, moved in accordance with the foregoing, and even operated using a single hand of a clinician, which, in turn, leaves another hand of the clinician free for other related operations such as placing a medical device such as VAD (e.g., a needle, a catheter, etc.) in an anatomical target under the probe head 106 or 206. The handle 110 can include a knob as shown; however, the handle 110 can alternatively include one or more finger loops, an adjustable touch-fastener hand strap, or the like. Notably, when the handle 110 is the knob, the knob can be configured to pop out from the case 104 or 204 such as from a complementarily dimensioned posterior compartment of the case 104 or 204 prior to using the portable ultrasound system 100 or 200. The knob can be further configured to pop back into the case 104 or 204 or the posterior compartment thereof after using the portable ultrasound system 100 or 200. In this way, the handle 110 of the portable ultrasound system 100 or 200 can have a smaller form factor when not being used for ultrasound imaging such as for inputting textual or graphical data in keeping patients' medical records current.

The case can 104 or 204 include a rechargeable battery 112 integrated into the case 104 or 204 opposite the anterior opening. The battery 112 is configured to provide main or backup power to the portable ultrasound system 100 or 200 including the handheld computer 102, the array of ultrasonic transducers 116, the array of magnetic sensors 118, or the like.

The probe head 106 can be removably coupled to the case 104 as shown in FIGS. 1A-1C, and the probe head 206 can be fixedly coupled to the case 204 as shown in FIGS. 3A-3C. As the probe head 106 is removably coupled to the case 104, the probe head 106 can be advantageously swapped out for another probe head when needed. In an example, the probe head 106 might be a curvilinear probe head useful for abdominal applications when a linear probe head is needed for vascular applications. The probe head 106 being removably coupled to the case 104 allows the curvilinear probe head to be swapped out for the linear probe head or vice versa if the curvilinear probe head is needed over the linear probe head. The removably coupled probe head 106 can be further advantageously configured to articulate. Indeed, the removably coupled probe head 106 can be configured to articulate in any direction about a joint 114 (e.g., ball joint) coupling the probe head 106 to the case 104. That said, the fixedly coupled probe head 206, too, can be advantageously configured to articulate as well.

The probe head 106 or 206 includes an array of ultrasonic transducers 116 disposed therein such as in a linear array, a curvilinear array, or a 2D array of ultrasonic transducers. The ultrasonic transducers of the array of ultrasonic transducers 116 can be piezoelectric ultrasonic transducers or capacitive micromachined ultrasonic transducers ("CMUTs"). Regardless, the array of ultrasonic transducers 116 in the probe head 106 or 206 can emit generated ultrasound signals into a patient, receive reflected ultrasound signals from the patient, and convert the reflected ultrasound signals into corresponding electrical signals for processing into ultrasound images by the handheld computer 102.

The probe head 106 or 206 can include an array of magnetic sensors 118 (e.g., Hall-effect sensors) disposed therein for detecting a magnetized medical device such as a magnetized VAD (e.g., a magnetized needle) when the magnetized medical device is proximate the array of magnetic sensors 118. The array of magnetic sensors 118 is configured to detect a magnetic field or a disturbance in a magnetic field as magnetic signals associated with the magnetized medical device. The array of magnetic sensors 118 is also configured to convert the magnetic signals from the magnetized medical device into electrical signals for the handheld computer 102 to process into distance and orientation information for the magnetized medical device with respect to a selected anatomical target under simultaneous ultrasound imaging. Advantageously, such distance and orientation information for the magnetized medical device can be used to provide haptic feedback or display an iconographic representation 133 of the magnetized medical device on the display screen of the display 132 of the handheld computer 102 for guided insertion of the magnetized medical device into the anatomical target.

The portable ultrasound probe can further include a needle guide 120 removably coupled to a needle-guide holder 122 of the probe head 106 or 206. The needle guide 120 includes a needle through hole configured to direct a needle disposed therein into a selected anatomical target of a patient under the probe head 106 or 206.

The communicating means for communicating between the probe head 106 or 206 and the handheld computer 102 can be wired or wireless. In an example, the communicating means for communicating between the probe head 106 or 206 and the handheld computer 102 can be a bus between the probe head 106 or 206 and a connector (e.g., a micro universal serial bus ["USB"] connector, a USB Type-C connector, etc.) disposed in the case 104 or 204 for connecting the handheld computer 102 when the handheld computer 102 is removable from the case 104 or 204. When the handheld computer 102 is integral with the case 104 or 204, however, the bus can directly connect the probe head 106 or 206 and the handheld computer 102 for communications therebetween. In another example, the probe head 106 or 206 includes a wireless module 123 disposed therein for wireless communications with a wireless module 125 of the handheld computer 102. Notably, the wireless module 125 of the handheld computer 102 can be further configured for wireless communications with one or more remote computers for remote image processing or external display such that an external display of the one-or-more computers can duplicate or supplant the display 132 of the portable ultrasound system 100 or 200.

The handheld computer 102 can be a dedicated device or a smartphone configured for ultrasound imaging. Indeed, whether the handheld computer 102 is a dedicated device or a smartphone, the handheld computer 102 is configured to drive the array of ultrasonic transducers 116 as well as process reflected ultrasound signals received by the array of ultrasonic transducers 116 into ultrasound images for display on the display screen of the display of the handheld computer 102. Such configuration can be accomplished by hardware, software, or a combination thereof In an example, the dedicated device can include hardware for signal processing of the reflected ultrasound signals, whereas the smartphone can include software (e.g., one or more programs or modules thereof) for signal processing of the reflected ultrasound signals. As such, it should be understood components of the handheld computer 102 shown in FIG. 5 and set forth below can vary between the dedicated device and the smartphone, particularly with respect to the combination of hardware and software for the ultrasound imaging.

As shown, the handheld computer 102 includes one or more processors 124, primary memory 126 including volatile memory such as random-access memory ("RAM") and non-volatile memory such as read-only memory ("ROM"), and secondary memory 128 including non-volatile memory such as flash memory (e.g., one or more flash-memory chips in combination with a flash-memory controller chip, optionally in a memory card, solid-state drive, etc.), wherein the primary memory 126 is directly accessible by the one-or-more processors 124 and the secondary memory 128 is not directly accessible by the one-or-more processors.

Instructions 130 stored in the primary memory 126, the secondary memory 128, or a combination thereof are configured to instantiate one or more programs or modules thereof in the RAM for ultrasound imaging. The one-or-more programs or modules thereof can include those for driving the array of ultrasonic transducers 116; processing reflected ultrasound signals received by the array ultrasonic transducers 116 into ultrasound images; processing magnetic signals received by the array of magnetic sensors 118 into distance and orientation information for on-screen guidance of magnetized medical devices to anatomical targets; or providing a graphical user interface ("GUI") 135, an ultrasound image viewer, or the on-screen guidance for the magnetized medical devices to the anatomical targets for display on a display screen of a display 132 of the handheld computer 102. In an example, the one-or-more programs or modules thereof can include a beamformer 134 configured to drive the array of ultrasonic transducers 116 as well as receive, amplify, and digitize the reflected ultrasound signals; a signal processor 136 configured to detect an amplitude of each of the foregoing reflected ultrasound signals or the digitized signals corresponding thereto; and an image processor 138 configured to manage storage of detected amplitudes and send ultrasound images corresponding to collections of the detected amplitudes to the display screen of the display 132 upon completion of the ultrasound images for viewing in the ultrasound image viewer. However, it should again be emphasized the one-or-more programs or modules thereof for the ultrasound imaging can alternatively be implemented in hardware.

On-screen buttons 137 provided by the GUI 135, an optional microphone 140, a camera 142, and the one-or-more side buttons 108 or those of the handheld computer 102, itself, provide various user interfaces by which a clinician can input textual or graphical data before, during, or after ultrasound imaging with the portable ultrasound system 100 or 200. The textual data can include text entered by way of typing on an on-screen keyboard, selected by way of one or more graphical control elements (e.g., the on-screen buttons 137, drop-down lists, etc.), dictated into the microphone 140 and processed through voice recognition software, captured by the camera 142 from one-dimensional ("1D") or 2D barcodes, or the like. The graphical data can include images or videos captured with the camera 142. Such textual or graphical data can be useful for effectively utilizing the portable ultrasound system 100 or 200. For example, the textural or graphical data can include technical details for the magnetized medical device useful in providing accurate on-screen guidance while placing the magnetized medical device in an anatomical target. The textual or graphical data can also be useful in keeping patients' medical records (e.g., electronic health records ["EHRs"]) current with respect to patient identification, medication, blood samples, catheter flushes, wound-dressing changes, potential complications, etc. Advantageously, when the handheld computer 102 is removable, the handheld computer 102 can be removed from the portable ultrasound system 100 or 200 for a smaller form factor for input of the foregoing textual or graphical data. Likewise, the probe head 106 can decoupled from the case 104 for a smaller form factor for input of the textual or graphical data.

Notably, at least the on-screen buttons 137 provided by the GUI 135 and the one-or-more side buttons 108 or those of the handheld computer 102, itself, can further provide quick controls for switching among various functions or modes of the portable ultrasound system 100 or 200. In an example, the foregoing buttons can be configured to further provide a quick control for switching between longitudinal and transverse views corresponding to the longitudinal and transverse scanning afforded by the 2D array of ultrasonic transducers, when present, in the probe head 106 or 206 or even switching into a split screen showing both the longitudinal and transverse views. In another example, the foregoing buttons can be configured to further provide a quick control for switching between different modes of the portable ultrasound system 100 or 200 including an initial assessment mode for assessing one or more potential anatomical targets for placement of a medical device (e.g., a catheter) therein, a placement or insertion mode for placing a precursory medical device (e.g., a needle) in a selected anatomical target, a subsequent assessment mode for assessing placement of the medical device (e.g., the catheter) in the anatomical target, or a data entry mode to input the foregoing textual or graphical data.

While not shown, the portable ultrasound system 100 or 200 can further include a wired or wireless charging cradle configured to charge the battery 112.

Advantageously, the portable ultrasound system 100 or 200 can be used to visualize potential anatomical targets (e.g., blood vessels) in preparation for placing a medical device in one of the potential anatomical targets. The portable ultrasound system 100 or 200 can also be used to visualize a selected anatomical target while placing the medical device therein, notably with on-screen guidance on the display screen of the display 132 of the handheld computer 102 if the medical device is magnetized and the array of magnetic sensors 118 are present in the probe head 106 or 206. Notably, image processing can be used to determine if the magnetized medical device is expected to intersect with a cross section of the selected anatomical target for successful placement therein. If not, the handheld computer 102 can generate notifications (e.g., haptic feedback, one or more visual notifications, one or more aural notifications through a speaker of the handheld computer 102, etc.) to a clinician. Fortunately, with the display 132 of the portable ultrasound system 100 or 200 at patient level proximate the anatomical site and the medical device to be placed therein, a clinician need not look away from the patient and across a room at another display while placing the medical device, thereby minimizing placement difficulties.

Methods

Methods of the portable ultrasound systems 100 and 200 include methods of using the portable ultrasound systems 100 and 200. For example, a method of using the portable ultrasound system 100 or 200 includes one or more steps selected from an obtaining step, a replacing step, an attaching step, a moving step, a monitoring step, a pressing step, a creating step, an imaging step, another monitoring step, and a placing step.

The obtaining step includes obtaining the portable ultrasound system 100 or 200. As set forth above, the portable ultrasound system 100 or 200 includes the handheld computer 102 including the display 132, the case 104 or 204 holding the handheld computer 102, and the probe head 106 or 206 coupled to the case 104 or 204.

The replacing step includes removing the probe head 106 from the case 104 and coupling another probe head to the case 104. For example, the probe head 106 might be a curvilinear probe head useful for abdominal application when a linear probe head is needed for vascular applications.

The attaching step includes attaching the needle guide 120 to the needle-guide holder 122 of the probe head 106 or 206. As set forth above, the needle guide 120 includes the needle through hole configured to direct the needle into a patient under the probe head 106 or 206.

The moving step includes moving the probe head 106 or 206 of the portable ultrasound system 100 or 200 over skin of the patient. For the probe head 106, the moving step also includes allowing the probe head 106 to articulate about the joint 114 coupling the probe head 106 to the case 104. While performing the moving step, the probe head 106 or 206 emits generated ultrasound signals into the patient from the array of ultrasonic transducers 116 in the probe head 106 or 206 and receives reflected ultrasound signals from the patient by the array of ultrasonic transducers 116. Advantageously, the portable ultrasound system 100 or 200 and the probe head 106 or 206 thereof can be moved in the moving step with a single hand. As set forth above, the case 104 or 204 includes the handle 110 selected from the knob, the one-or-more finger loops, and the adjustable strap configured to facilitate holding the portable ultrasound system 100 or 200 or moving the probe head 106 or 206 thereof over the skin of the patient with the single hand.

The monitoring step includes monitoring ultrasound images on the display screen of the display 132 of the handheld computer 102.

The pressing step includes pressing a side button of the one-or-more side buttons 108 of the case 104 or 204 to switch between longitudinal and transverse scanning when the array of ultrasonic transducers 116 is the 2D array of ultrasonic transducers.

The creating step includes identifying an anatomical target of the patient and inserting the needle into the anatomical target, thereby creating an access site.

The imaging step included imaging the skin of the patient through the posterior opening of the case 104 or 204 with the camera 142 of the handheld computer 102 after identifying the anatomical target thereunder and before inserting the needle into the anatomical target.

The other monitoring step includes monitoring on-screen guidance of the needle on the display screen of the display 132 of the handheld computer 102. The probe head 106 or 206 further includes the array of magnetic sensors 118 configured to detect changes in a magnetic field, when the needle is magnetized, for the on-screen guidance.

The placing step includes placing the portable ultrasound system 100 or 200 in the charging cradle to charge the battery 112 integrated into the case 104 or 204 of the portable ultrasound system 100 or 200.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A portable ultrasound probe, comprising:
   a case configured to removably hold a handheld computer, the case including:
      a posterior opening configured to frame a camera of the handheld computer;
      an anterior opening configured to frame a display of the handheld computer; and
      a rechargeable battery integrated into the case opposite the anterior opening;
   a probe head coupled to the case, the probe head including an array of ultrasonic transducers powered by the rechargeable battery;
   a needle guide coupled to a needle-guide holder of the probe head,
      the camera of the handheld computer configured to capture textual data from one-dimensional or two-dimensional barcodes and graphical data at any time, including before ultrasound imaging, with the portable ultrasound probe,
      the textual data and graphical data including technical details of a needle for accurate on- screen guidance on a display screen of the display when inserting the needle into an anatomical target under the probe head using the needle guide; and
   a communicating means for communicating between the probe head and the handheld computer.

2. The portable ultrasound probe of claim 1, wherein the case includes one or more side buttons configured to overlie one or more side buttons of the handheld computer, the one-or-more side buttons of the case configured to mechanically transfer button presses to the one-or-more side buttons of the handheld computer.

3. The portable ultrasound probe of claim 1, wherein the case includes a handle selected from a knob, one or more finger loops, or an adjustable hand strap incorporated into the case opposite the anterior opening, the handle configured to facilitate holding the portable ultrasound probe or moving the portable ultrasound probe over skin of a patient with a single hand.

4. The portable ultrasound probe of claim 1, wherein the probe head is removably coupled to the case.

5. The portable ultrasound probe of claim 1, wherein the probe head is fixedly coupled to the case.

6. The portable ultrasound probe of claim 1, wherein the probe head is configured to articulate about a joint coupling the probe head to the case.

7. The portable ultrasound probe of claim 1, wherein the communicating means for communicating between the probe head and the handheld computer is a wireless module disposed in the probe head for wireless communications with the handheld computer.

8. The portable ultrasound probe of claim 1, wherein the communicating means for communicating between the probe head and the handheld computer is a bus between the probe head and the handheld computer.

9. A portable ultrasound system, comprising:
   a handheld computer including a display;
   a case configured to removably hold the handheld computer, the case including:

a posterior opening configured to frame a camera of the handheld computer;

an anterior opening framing the display of the handheld computer; and a rechargeable battery integrated into the case opposite the anterior opening;

a probe head coupled to the case, the probe head including an array of ultrasonic transducers powered by the rechargeable battery;

a needle guide coupled to a needle-guide holder of the probe head, the camera of the handheld computer configured to capture textual data from one-dimensional or two-dimensional barcodes and graphical data at any time, including before ultrasound imaging, with the portable ultrasound system, the textual data and graphical data including technical details of a needle for accurate on-screen guidance on a display screen of the display when inserting the needle into an anatomical target under the probe head using the needle guide; and a communicating means for communicating between the probe head and the handheld computer.

10. The portable ultrasound system of claim 9, wherein the case includes one or more side buttons overlying one or more side buttons of the handheld computer, the one-or-more side buttons of the case configured to mechanically transfer button presses to the one-or- more side buttons of the handheld computer.

11. The portable ultrasound system of claim 9, wherein the case includes a handle selected from a knob, one or more finger loops, or an adjustable hand strap incorporated into the case opposite the anterior opening, the handle configured to facilitate holding the portable ultrasound system or moving the portable ultrasound system and the probe head thereof over skin of a patient with a single hand.

12. The portable ultrasound system of claim 9, wherein the probe head is removably coupled to the case.

13. The portable ultrasound system of claim 9, wherein the probe head is fixedly coupled to the case.

14. The portable ultrasound system of claim 9, wherein the probe head is configured to articulate about a joint coupling the probe head to the case.

15. The portable ultrasound system of claim 9, wherein the communicating means for communicating between the probe head and the handheld computer is a wireless module disposed in the probe head for wireless communications with a wireless module disposed in the handheld computer.

16. The portable ultrasound system of claim 9, wherein the handheld computer is a smartphone including one or more programs or modules thereof configured to drive the ultrasonic transducers and process reflected ultrasound signals received by the ultrasonic transducers into ultrasound images for display on a display screen of the display.

17. The portable ultrasound system of claim 9, wherein the handheld computer is a dedicated device configured to drive the ultrasonic transducers and process reflected ultrasound signals received by the ultrasonic transducers into ultrasound images for display on a display screen of the display.

18. The portable ultrasound system of claim 9, wherein the communicating means for communicating between the probe head and the handheld computer is a bus between the probe head and the handheld computer when the handheld computer is disposed in the case.

19. The portable ultrasound system of claim 9, wherein the handheld computer is integral, the handheld computer being a dedicated device configured to drive the ultrasonic transducers and process reflected ultrasound signals received by the ultrasonic transducers into ultrasound images for display on a display screen of the display.

20. The portable ultrasound system of claim 19, wherein the communicating means for communicating between the probe head and the handheld computer is a bus between the probe head and the handheld computer.

21. The portable ultrasound system of claim 9, further comprising a charging cradle configured to charge the rechargeable battery.

22. The portable ultrasound system of claim 9, the probe head further including an array of magnetic sensors disposed therein for detecting the needle when the needle is proximate the array of magnetic sensors.

23. The portable ultrasound system of claim 22, wherein the array of magnetic sensors is configured to convert magnetic signals from the needle into electronic signals for the handheld computer to process into distance and orientation information for an iconographic representation of the needle on the display screen of the display during the on-screen guidance.

24. The portable ultrasound system of claim 23, wherein the handheld computer is configured to generate notifications selected from haptic feedback, visual notifications on the display screen, and aural notifications through a speaker of the handheld computer if the needle is not expected to intersect with a cross section of the anatomical target in accordance with the distance and orientation information.

25. The portable ultrasound probe of claim 2, wherein one-or-more side buttons of the handheld computer are configured to provide controls for switching among various functions or modes of the portable ultrasound probe including switching between longitudinal and transverse views corresponding to longitudinal and transverse scanning or switching into a split-screen view showing both the longitudinal and transverse views.

* * * * *